United States Patent [19]

Boutacoff et al.

[11] Patent Number: 5,037,421
[45] Date of Patent: Aug. 6, 1991

[54] MID-INFRARED LASER ARTHROSCOPIC PROCEDURE

[75] Inventors: Theodore A. Boutacoff, Los Altos; David M. Buzawa, San Jose; Thomas S. Nelson, Stanford, all of Calif.

[73] Assignee: Coherent, Inc., Medical Group, Palo Alto, Calif.

[21] Appl. No.: 626,388

[22] Filed: Dec. 12, 1990

Related U.S. Application Data

[63] Continuation of Ser. No. 418,942, Oct. 6, 1989, abandoned, which is a continuation of Ser. No. 234,307, Aug. 19, 1988, abandoned.

[51] Int. Cl.$^5$ .............................................. A61B 17/36
[52] U.S. Cl. ...................................... 606/15; 128/395
[58] Field of Search .............................. 128/395–398; 606/3, 13–16; 372/41

[56] References Cited

U.S. PATENT DOCUMENTS

| 4,233,493 | 11/1980 | Nath | 128/303.1 |
|---|---|---|---|
| 4,330,763 | 5/1982 | Esterowitz et al. | 372/41 |
| 4,537,193 | 8/1985 | Tanner | 606/15 |
| 4,551,129 | 11/1985 | Coleman et al. | 128/303.1 |
| 4,564,011 | 1/1986 | Goldman | 606/15 |
| 4,608,980 | 9/1986 | Aihara | 128/303.1 |
| 4,627,435 | 12/1986 | Hoskin | 128/303.1 |
| 4,641,912 | 2/1987 | Goldenberg | 606/15 |
| 4,671,273 | 1/1987 | Lindsey | 128/398 |
| 4,693,244 | 9/1987 | Daikuzono | 128/303.1 |
| 4,718,417 | 1/1988 | Kittrell et al. | 128/303.1 |
| 4,785,806 | 11/1988 | Deckelbaum | 128/303.1 |

FOREIGN PATENT DOCUMENTS

| 0214712 | 3/1987 | European Pat. Off. | 128/303.1 |
|---|---|---|---|
| 0248520 | 12/1987 | European Pat. Off. | 128/303.1 |
| 82/02604 | 8/1982 | World Int. Prop. O. | 128/398 |
| 85/05263 | 12/1985 | World Int. Prop. O. | 128/303.1 |

OTHER PUBLICATIONS

R. J. Lane, C. A. Puliafito, R. Margolis, "Holmium Laser (2.06 μm) Tissue Ablation"; Laser Research Laboratory, Massachusetts Eye and Ear Infirmary, Wellman Laboratory, Mass., General Hospital, Harvard Medical School, Boston, MA., Jun. 1986.

R. J. Lane, C. A. Puliafito, "Comparative Study of the Surgical Application of the Holmium and CO$_2$ Lasers", Lasers in Surgery and Medicine, vol. 6, No. 2, 1986.

Glick, "Use of Laser Beam in Arthroscopic Surgery", article, Mar. 1983.

Primary Examiner—Max Hindenburg
Attorney, Agent, or Firm—Limbach, Limbach & Sutton

[57] ABSTRACT

A Ho:YAG laser is coupled to a needle tip through a flexible, fiber optic cable for performing endoscopic and arthroscopic surgery.

6 Claims, 1 Drawing Sheet

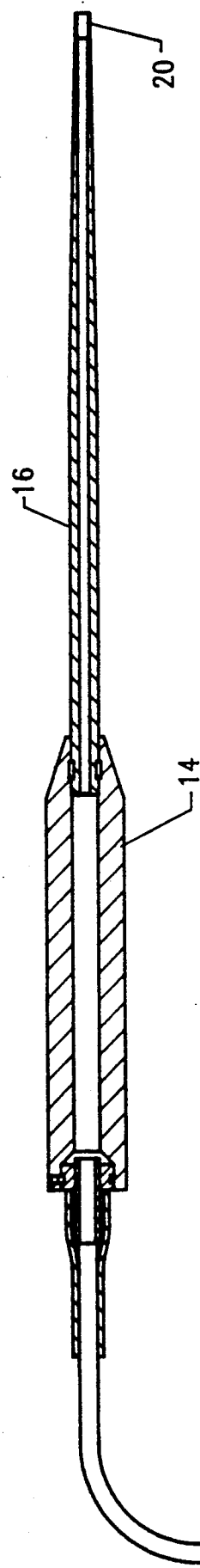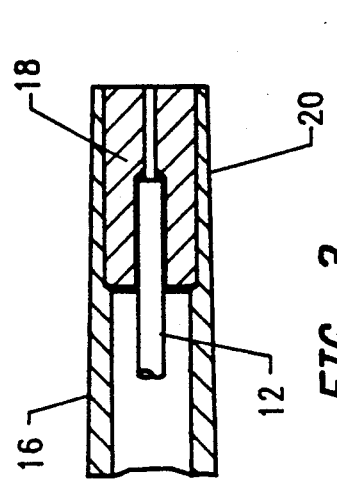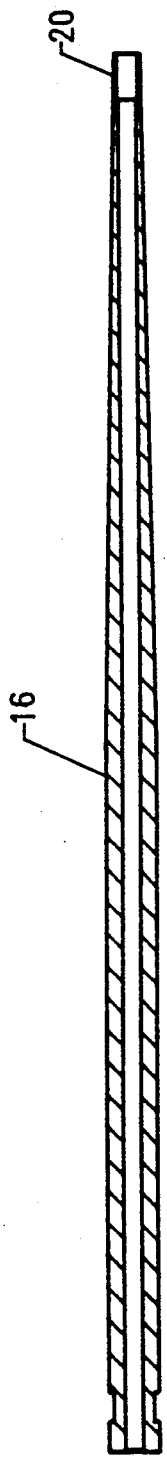

MID-INFRARED LASER ARTHROSCOPIC PROCEDURE

This is a continuation of application Ser. No. 07/418,942 filed on Oct. 6, 1989 abandoned, which was in turn a continuation of application Ser. No. 07/234,307 filed on Aug. 19 1988, abandoned.

TECHNICAL FIELD

This invention relates to endoscopes and more particularly to a mid-infrared laser endoscope for use in performing arthroscopy.

BACKGROUND ART

For over fifteen years, laser energy has been used routinely in major and minor surgical procedures. Safety and efficacy have been proven for applications in plastic surgery, dermatology, ophthalmology, otolaryngology, neurological surgery, obstetrics and gynecology, gastroenterology, urology, and general surgery. With the development of rigid and flexible endoscopic surgical techniques, there has been parallel interest in endoscopically-guided laser surgery. In many endoscopic procedures, including arthroscopy, pathological tissue may be confined to relatively inaccessible spaces, and a laser surgery technique would greatly facilitate removal of these lesions.

There are potential advantages to utilizing laser energy for arthroscopic meniscectomy, which has become one of the most frequency performed orthopedic procedures in the United States and Canada. With conventional arthroscopic meniscectomy, the mechanical instrumentation is cumbersome in the rigid confines of the knee, and often causes scuffing or gouging of the articular cartilage. Also, the small instruments used to cut relatively dense tissue have resulted in instrument failure and breakage within the joint during the course of the procedure. Focussing a laser beam between the rigid, confining articular surfaces of the knee permits remote access to torn or degenerated meniscus tissue with a decreased risk of iatrogenic injury to the articular cartilage as seen with the rigid instruments presently employed.

Previously, injuries to and degenerative lesions of the meniscus in the knee were treated by total meniscectomy. Even suspected lesions of the meniscus frequently resulted in total meniscectomy. It has been demonstrated in long term follow-up studies of patients with total meniscectomies, that a premature incidence of degenerative arthritis in the knee occurs. This led to the development of high quality arthroscopes which provide intra-articular illumination via fiber optic light bundles permitting the resection of only the structurally damaged portions of the meniscus. The use of the laser allows for greater ease with a partial meniscectomy procedure which tries to retain a functional peripheral rim of meniscus.

The focus of most laser arthroscopy investigations has been with use of the carbon dioxide laser system. However, the inherent properties of the $10.6\mu$ wavelength lasers have not allowed for development of the carbon dioxide lasers as an effective or convenient laser arthroscopic system. This wavelength cannot be readily transmitted by standard fiber optics. Instead, the system must be used with larger rigid endoscopes. The arthroscopic delivery system must be connected to the laser source through a cumbersome articulated arm which limits the surgical fields that are accessible for treatment. However, experiments have been performed to show that a Nd:YAG laser can be coupled through a fiber optic cable to perform laser surgery on a meniscus.

A significant disadvantage of the carbon dioxide laser for meniscectomy is that its wavelength is not readily transmitted via optical fiber; and since it is readily absorbed by water the surgeon must use gas distention of the joint rather than the safer saline infusion procedure. During a conventional arthroscopic procedure, the joint is distended with a saline solution. All instrumentation and viewing systems are adapted to the fluid environment. Thus, the need to distend the joint with gas for the $CO_2$ laser creates an array of complications and reduces the attractiveness of this laser to the physician. In a gaseous medium, smoking of the tissue during ablation often clouds the viewing lens and requires flushing the joint with saline. When nitrogen is employed, gas reabsorbed by the tissue during the procedure may cause swelling lasting up to one week postoperatively. In addition, maintaining distention of the joint is often difficult if several portholes are employed.

Similarly, Nd:YAG lasers have been tried to perform arthroscopic meniscectomies, but though the $1.064\mu$ laser light is deliverable through standard optical fibers, the meniscus is quite transparent to the Nd:YAG wavelength and much of the energy is not absorbed. Effective ablation of meniscal tissue requires better coupling and a shorter absorption depth than is available from the Nd:YAG laser.

DISCLOSURE OF INVENTION

The above and other problems of prior laser endoscopes are overcome by the present invention of a laser endoscope comprising a mid-infrared laser, a semirigid, fiber optic tip, a handle for mounting the tip, and a flexible fiber cable connecting the laser to the tip. In the current embodiment, the laser of choice is a solid state laser with an output between 1.8 and $2.2\mu$ a spectral region characterized by efficient absorption by water and any hydrated biological tissues.

Although the carbon dioxide lasers have been proven safe and effective for partial meniscectomy of the knee, the Ho:YLF (virtually the same laser wavelength as the Ho:YAG) laser has proven to be equivalent, if not superior, to carbon dioxide lasers in both in vitro and in vivo comparative studies. The results of these studies demonstrate that the Ho:YLF and Ho:YAG lasers are capable of producing carbon dioxide laser-like ablation craters in autopsy specimens, bovine meniscus, sclera, and cornea with a substantial equivalence in thermal damage to the surrounding tissue. The major difference between the Ho:YLF laser and the carbon dioxide laser is that the Ho:YLF can produce effective laser ablations in a fluid field instead of a dry field found in the laser delivery of carbon dioxide lasers. The tissue cutting properties, coupled with the ability to transmit laser radiation through a conventional quartz optical fiber, which cannot be accomplished with the carbon dioxide laser, and the ability for laser delivery in a fluid environment show the solid state lasers having a wavelength of 1.8 to $2.2\mu$ to be effective surgical tools.

The foregoing and other objectives, features and advantages of the invention will be more readily understood upon consideration of the following detailed description of certain preferred embodiments of the invention, taken in conjunction with the accompanying drawings.

BRIEF DESCRIPTION OF THE DRAWINGS

FIG. 1 is a diagrammatic view, partly in section, of the laser endoscope system according to the invention;

FIG. 2 is an enlarged, vertical sectional view of the needle of the laser endoscope system shown in FIG. 1; and FIG. 3 is an enlarged detail of FIG. 2.

BEST MODE FOR CARRYING OUT THE INVENTION

Referring now to FIG. 1, a holmium:yttrium-aluminum-garnet (Ho:YAG) laser 10 is used as the light source. The laser could be, for example, a Ho:YAG surgical laser (2.1μ wavelength). A focusing lens (not shown) couples the laser energy to a low OH dry silica fiber 12 of suitable core diameter. Such a fiber might be, for example, a 200-600 micron diameter, low-OH, silica optic fiber. It has also been found that at plastic clad silica ("PCS") fiber of the same diameter range is effective. The fiber typically produces no more than a 15% transmission loss over lengths of ten meters. For delivery of laser energy to the tissues, the fiber 12 is mounted in a shaft 16 of suitable gauge, with a surgical handle 14 attached. FIG. 3 illustrates the output tip 20 of the endoscope. As shown therein, the delivery end of the fiber 12 is reduced in diameter and is received in and supported by a fitting 18. The output tip 20 is used in direct or near direct contact with the target tissue. Direct contact maximizes ablation efficiency and minimizes thermal damage to adjacent tissue structures. The tip 20 may be deliberately backed away from the target tissue to obtain a hemostatic effect when desired.

Additionally, beam shaping may be conveniently accomplished by the use of microlens output tips, either comprised of discrete parts or formed from or attached to the output end of the fiber 12. Lenses may be glass or silica or refractory material such as diamond or sapphire to resist erosion during use.

To summarize, the Ho:YAG laser is equivalent in safety and effectiveness to carbon dioxide lasers which have been approved by the FDA for meniscectomy. It has many potential advantages to the carbon dioxide laser for arthroscopic treatment including: 1) readily connects to a standard quartz fiber optic cable which allows for the use of a small, convenient delivery system; 2) the fiber can be placed in direct contact with tissues, enabling the treatment beam to be aimed with great accuracy; 3) the surgeon can readily adapt to the system because it resembles their same familiar tactile systems; 4) the Ho:YAG is effective in a water medium, therefore, fluids may be used to flush the knee rather than various gases, reducing the amount of smoke produced during the procedure which improves visualization and safety; 5) The Ho:YAG laser wavelength is more effective for coagulation than the carbon dioxide wavelength.

While the invention has been described with respect to a Ho:YAG laser source, it should be understood that in other embodiments other solid state laser sources with an output wavelength of between 1.8 and 2.2μ could be used. These lasers exhibit the same tissue ablation effects.

Although the present invention has been shown and described with respect to preferred embodiments, various changes and modifications which are obvious to a person skilled in the art to which the invention pertains are deemed to lie within the spirit and scope of the invention.

What is claimed as the invention is:

1. A method of performing an arthroscopic procedure comprising the steps of:
   generating a laser beam having a wavelength of between 1.8 and 2.2 microns;
   directing the beam into one end of a fiber optic cable, with the other end of the fiber optic cable defining the delivery end thereof;
   positioning the delivery end of the fiber optic cable adjacent the tissue to be ablated by the laser beam; and
   irrigating the tissue with a liquid medium as it is being ablated by a laser beam.

2. A method as recited in claim 1 wherein the laser beam is generated by a Ho:YAG laser.

3. A method as recited in claim 1 wherein the laser beam is generated by a Ho:YLF laser.

4. A method as recited in claim 1 wherein the fiber optic cable is a 200-600 micron diameter, low-OH, silica optic fiber.

5. A method as recited in claim 1 wherein the fiber optic cable is a 200-600 micron diameter, plastic clad silica optic fiber.

6. A method as recited in claim 1 wherein the delivery end of the fiber optic cable is threaded through and supported by a fitting.

* * * * *